United States Patent
Whitekettle et al.

(10) Patent No.: US 6,579,859 B1
(45) Date of Patent: Jun. 17, 2003

(54) CONTROL OF PROTOZOA AND PROTOZOAN CYSTS THAT HARBOR LEGIONELLA

(75) Inventors: Wilson K. Whitekettle, Jamison, PA (US); Gloria J. Tafel, Doylestown, PA (US)

(73) Assignee: GE Betz, Inc., Trevose, PA (US)

( * ) Notice: Subject to any disclaimer, the term of this patent is extended or adjusted under 35 U.S.C. 154(b) by 0 days.

(21) Appl. No.: 10/165,917

(22) Filed: Jun. 10, 2002

(51) Int. Cl.$^7$ ............................................... A61K 31/66
(52) U.S. Cl. ......................................... 514/77; 424/601
(58) Field of Search ............................. 514/77; 424/601

(56) References Cited

PUBLICATIONS

Berk, S. G., Ashburn, R.J. and Ting R.S., "Aspects of Cooling Tower Biocides and Protozoa," NACE International Corrosion 98, Paper No. 527, 1998.

Berk, S.G., Ting, R.S., Turner, G.W., and Ashburn, R.J., "Production of Respirable Vesicles Containing Live Legionella pneumophila Cells by Two Acanthamoeba spp.," Applied and Environmental Microbiology, vol. 64, No. 1, 279–286, 1998.

Harb, O.S., and Kwaik, Y.A., "Interation of *Legionella pneumophila* with Protozoa Provides Lessions.," ASM News, vol. 66, No. 10, 609–616, 2000.

Kilvington S., "Activity of Water Biocide Chemicals and Contact Lens Disinfectants on Pathogenic Free—Living Amoebae," International Biodeterioration, 26, 127–138, 1990.

Kilvington S., and Price, J. Survival of *Legionella pneumophila* within cysts of Acanthamoeba polyphaga., Journal Of Applied Bacteriology, 68 519–525, 1990.

Sriknath, S., and Beck, S.G., "Adaptation of Amoebae to Cooling Tower Biocides," 27, 293–301, 1994.

Sriknath S., and Beck, S.G. "Stimulatory Effect of Cooling Tower Biocides on Amoebae," 59, No. 10, 3245–3249, 1993.

Sutherland, E. E. and Berk, S. G., Survival of Protozoa in Cooling Tower Biocides, Journal of Industrial Microbiology 16, 73–78, 1996.

*Primary Examiner*—Phyllis G. Spivack
(74) *Attorney, Agent, or Firm*—Steven D. Boyd

(57) ABSTRACT

A method of controlling protozoa trophozoite and cysts is disclosed, comprising administering a phosphonium salt of the formula: $(R_1)_3P^-R_2.X^-$, wherein $R_1$ is an alkyl group having from 1–8 carbons and $R_2$ is a chain substituent having 6–20 carbons, to aqueous systems harboring protozoa trophozoites and cysts. Addition of such phosphonium salts to aqueous systems was found to be effective at killing both the protozoa trophozoites and cysts. By effectively killing both the protozoa trophozoites and cysts, organism such as Legionella cells harbored in both the trophozoites and cysts are killed.

7 Claims, No Drawings

CONTROL OF PROTOZOA AND PROTOZOAN CYSTS THAT HARBOR LEGIONELLA

FIELD OF THE INVENTION

The present invention relates to methods for controlling Legionella harboring protozoa trophozoites and cysts in aqueous systems. More particularly, the present invention relates to methods for controlling Legionella type bacteria engulphed within a protozoa in the trophozoite form or in Acanthamoeba in the trophozoite and cyst form. The methods of the present invention involve exposing the protozoa to phosphonium salts of the general formula:

$$(R_1)_3P^+R_2.X^-$$

Wherein $R_1$ is an alkyl group of from 1–8 carbon atoms, $R_2$ is an n-alkyl group having 8–20 carbon atoms and X is an anion consisting of a halide (such as $Cl^-$, $Br^-$, etc.), sulfate, nitrate, nitrite etc.

BACKGROUND OF THE INVENTION

Intracellular bacterial pathogens are a major cause of human morbidity and mortality. Evading hostile intracellular environments is one of the ways pathogens can live within a host cell, even grow within host cells, and yet not be killed or inhibited by the host cell. These parasites have developed ways of interacting and overcoming the host cells natural defense mechanisms. *Legionella pneumophila*, a bacterium known to cause Legionnaire's Disease and Pontiac fever in humans is a parasite of this type. While the Legionella cells can be killed while readily exposed to certain chemical agents and antibiotics, Legionella can also be found engulphed (phagocitized) within certain protozoa hosts. Legionella are often found in biofilms adsorbed to solid surfaces in water distribution systems, cooling towers, showers, aquaria, sprinklers, spas, and cleaning baths. Protozoa are natural grazers on surfaces and engulph and digest bacteria as part of their natural life cycle. In most cases, the protozoa digest these bacteria through the use of digestive enzymes in their phagosomes (digestive vacules). In the case of Legionella, however, this is not the case. The protozoa are not readily capable of degrading the engulphed Legionella cells, and in fact, the Legionella grow and increase their numbers while protected within protozoa phagosomes. Legionellosis in humans can be contracted by breathing Legionella aerosols containing either the free-living bacterial cells or by inhaling aerosols of Legionella concentrated within susceptible protozoa. A Legionella control agent, therefore, must be capable of killing free living Legionella, Legionella within protozoa, or the protozoa themselves. The agents described in this invention are capable of killing the free-living Legionella and the host protozoa. Two protozoa species capable of harboring infectious Legionella are Acanthamoeba and Tetrahymena.

In order to effectively control Legionella, in addition to killing the free-living or protozoa an additional factor must be taken into account. Certain protozoa, particularly amoeboid forms have evolved mechanisms for surviving in hostile environments. Examples of hostile environments are high temperature, desiccation, presence of chemical agents/antibiotics, lack of food sources, etc. Upon introduction of a hostile environment, these protozoa revert to a cyst form which is very difficult to kill. The cyst form becomes much less susceptible to chemical agents which readily kill the same organism when in it is in non-cyst (trophozoite) form. Introduction of a chemical control agent to eliminate Acanthamoeba can actually provide the hostile environment to which the protozoa responds by reverting to a cyst form, thereby rendering it invulnerable to the chemical agent. When the cyst contains the pathogen Legionella, the chemical agent can no longer reach the engulphed bacteria, and the chemical treatment is rendered ineffective. As an example, chlorination or bleach is considered essential to control Legionella in water distribution systems. Exposed Legionella are readily killed by low levels of free chlorine (0.2–0.5 $\mu$g/ml).

Legionella can also be contained in Acanthamoeba phagosomes if those protozoa are present. The Acanthamoeba sensing the chlorine presence, reverts to a cyst form, inadvertently preserving and protecting the Legionella parasites engulphed within it. Acanthamoeba cysts treated with >500 times (>100 $\mu$g/ml 'free' chlorine) the concentration needed to kill the trophozoite forms do not kill these cysts. The cysts can revert to the active trophozoite form upon removal of the oxidant. Currently there are no cyst deactivating (killing) agents in commercial use. Control agents that kill the Legionella harboring protozoa cysts would provide a much needed additional tool to safeguard the health of workers and the public against the respiratory pneumonias which can result from inhalation of Legionella or Legionella containing protozoan cysts.

DETAILED DESCRIPTION OF THE PREFERRED EMBODIMENTS

It has been discovered that unique phosphonium salts are effective at controlling Legionella type bacteria in the free living state as well as when engulphed in protozoa in the trophozoite form or Acanthamoeba in cyst form. The ability to control materials in the cyst form as well as the trophozoite form at comparable treatment levels is an unexpected feature of the treatment of the present invention.

It was discovered that the phosphonium salts of the general formula:

$$(R_1)_3P^+R_2.X^- \qquad \text{Formula I}$$

Wherein $R_1$ is an alkyl group having from 1–8 carbons, $R_2$ is an n-alkyl group having 6–20 carbon groups and $X^-$ is an anion such as halides, sulfates, nitrates, nitrites and mixtures thereof. Preferably, $X^-$ is chloride, bromide, iodide, $SO_4^=$, and $NO_3^=$, $NO_2^-$ or mixtures thereof. A preferred phosphonium salt is the chloride salt of:

$$[CH_3(CH_2)_3]_3 \, P^+(CH_2)_{13} \, CH_3.X^- \qquad \text{Formula II}$$

Wherein $X^-$ is $Cl^-$, $Br^-$, $I^-$, $SO_4^=$ or $NO_3^-$

The efficacy of the present invention was determined by evaluating the effect of a variety of treatments on the mortality of Tetrahymena, Acanthamoeba trophozoite, and Acanthamoeba cyst according to the following procedures.

Tetrahymena Toxicity Test Procedure

Tetrahymena cells from a commercial source were grown in PCB broth in a tissue culture flask. The cells were removed from the broth via centrifuge and suspended in Osterhout-tris buffer at a concentration of no greater than 60 cells per 10 micro liters. A standard 96 well test plate comprising successive 50% dilutions of this cellular solution per row was prepared. Chemicals to be tested were added to 3 adjacent wells. Organism viability was tested via observation through an inverted microscope at time zero and every 24 hours thereafter. Tetrahymena were judged viable if they were motile or had active contractile vacuoles. All organisms in a well had to be dead to have a negative reading. A positive reading indicated all or some viable orgasms in a well. The minimal lethal concentration (MLC) of the test materials to Tetrahymena was the lowest toxicant concentration in which all Tetrahymena were dead in all replicate wells.

Acanthamoeba Toxicity Test Procedure

E. coli (ATCC #25922) grown in Difco Bacto nutrient agar and killed via UV light were used as nutrient for the Acanthamoeba. The killed E. coli were placed on a non-nutrient agar plate. 1–2 drops of washed Acanthamoeba Trophozoite (from Tennessee Technological University) were placed on the plate and incubated for 2–3 days at 30° C. An inoculum was prepared by placing about 2 ml of Osterhout-tris buffer onto the 2–3 day old plates. A sterile loop was used to dislodge the Trophozoites from the agar surface. The liquid was transferred to a sterile tube and diluted 1:10. 10 micro liters were placed on a slide and counted to confirm about 90 Acanthamoeba per 10 micro liters for the test. This solution was placed in a standard 96 well test plate with successive 50% dilutions per row. A 400 ppm solution of toxicants in Osterhout-tris buffer was prepared. Toxicants were added to 3 adjacent wells for testing. To avoid cross contamination, a well was skipped between each 3 replicate wells in every row and every other row skipped on the plate. The plate was incubated at 30° for 24 hours. An inverted microscope was used to observe the organisms in the wells. Cytoplasm will move in live amoeba and/or the contractile vacuoles will remain active. All organisms had to be dead in a well to have a negative reading. The minimal lethal concentration (MLC) of the test toxicant was the toxicant concentration in which all organisms died in all replicate wells.

Acanthamoeba Cyst Toxicity Test Procedure

E. coli (ATCC#25922) were grown in Difaco Bacto nutrient agar and killed via UV light for use as nutrient for the Acanthamoeba cysts. The killed E. coli were placed on a non-nutrient agar plate. 1–2 drops of washed Acanthamoeba (from Tennessee Technological University) from a 2–3 day old plate were placed on the plate and incubated for 2–3 days at 30° C. A biofilm was prepared by placing approximately 9 milliliters of the active E. coli culture in sterile coplin jars containing 4 cover slips and incubating over night. The cover slips were rinsed in Osterhout-tris buffer and placed on 2–3 day old Acanthamoeba trophozoite plates and incubated for 7 days. In 7 days, the trophozoites will exhaust the E. coli nutrients and form cysts. The cover slips were soaked in approximately 9 milliliters of Osterhout-tris buffer and the cover slips placed in coplin jars. 50 ppm dilutions of the biocides to be tested were added to the coplin jars containing the cover slips with cysts and the coplin jars were incubated at 30° C. for 24 hours.

After 24 hours, the test solutions were removed and the cover slips soaked in Osterhout-tris buffer for 30 minutes. The cover slips were placed on non-nutrient agar plates with live E. coli. The plates were observed using an inverted microscope every day for 6 days to see if trophozoites were present. If trophozoites appeared, the test was positive. If no trophozoites appeared after 6 days, the test is negative (all cysts were killed). The test was repeated at different concentrations of treatment if the 50 ppm dilution was effective to determine the lower limit of efficacy.

TABLE I

| | Minimal Lethal Concentration (µg/ml) | | |
|---|---|---|---|
| Treatment | Tetrahymena (Trophozoite) | Acanthanoeba (Trophozoite) | Acanthamoeba (Cyst) |
| Control | +++ | +++ | +++ |
| TBTDPC | 2.5 | 2.5 | 40 |
| TBTDPC | 2.5 | 2.5 | 25 |
| TBTDPC | 2.5 | 2.5 | 25 |
| TBTDPC | — | — | 25 |
| TBTDPC | — | — | 25 |
| THPS | 28 | 56 | >50 |

TBTDP = Tri-n-butyl-tetradecylphosphonium chloride
THPS = Tetra kis hydroxymethyl phosphonium chloride The test results summarized in Table I show the minimal lethal concentration (MLC) in micrograms per milliliters (µg/ml) for replicate tests of the phosphonium salts: tri-n-butyl-tetradecylphosphonium chloride (TBTDPC) and, Tetra kis hydroxymethyl phosphonium chloride (THPS) for the Tetrahymena and Acanthanobea in the trophozoite stage and Acanthanobea in the cyst stage. The data shows that the phosphonium salt having a long chain substituent group ($R_2$=6–20) was effective at killing the protozoa in both the trophozoite and the cyst stage while the phosphonium salts having a short chain substituent group was relatively ineffective.

While the present invention has been described with respect to particular embodiments thereof, it is apparent that numerous other forms and modifications of the invention will be obvious to those skilled in the art. The appended claims and the present invention generally should be construed to cover all such obvious forms and modifications which are within the true spirit and scope of the present invention.

What is claimed is:

1. A method of controlling protozoa trophozoites and cysts comprising exposing said protozoa to an effective amount for killing said protozoa trophozoites and cysts of a phosphonium salt of the formula:

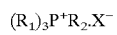

$(R_1)_3P^+R_2.X^-$ wherein $R_1$ is an alkyl group having from 1–8 carbons, $R_2$ is an n-alkyl group having from 6–20 carbon atoms and $X^-$ is an anion selected form the group consisting of halides, sulfates, nitrates, nitrites and mixtures thereof.

2. The method of claim 1 wherein said protozoa are in the trophozoite form.

3. The method of claim 1 wherein said protozoa are in the cyst form.

4. The method of claim 1 wherein said protozoa contain Legionella type bacteria.

5. The method of claim 1 wherein $X^-$ is selected from the group consisting of is $Cl^-$, $Br^-$, $SO_4^-$, $NO_3^-$, $NO_2^-$, $I^-$ or mixtures thereof.

6. The method of claim 1 wherein said phosphonium salt is added in a treatment concentration of from about 0.1 to 100 micrograms per milliliter.

7. The method of claim 1 wherein said phosphonium salt is Tri-n-butyl-tetradecylphosphonium chloride.

* * * * *